United States Patent
Weichert et al.

(10) Patent No.: US 6,703,411 B2
(45) Date of Patent: Mar. 9, 2004

(54) SUBSTITUTED BENZOYLGUANIDINES, PROCESS FOR THEIR PREPARATION, THEIR USE AS A MEDICAMENT OR DIAGNOSTIC, AND MEDICAMENT CONTAINING THEM

(75) Inventors: Andreas Weichert, Egelsbach (DE); Udo Albus, Florstadt (DE); Hans-Willi Jansen, Niedernhausen (DE); Heinz-Werner Kleemann, Bischofsheim (DE); Hans Jochen Lang, Hofheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/760,670

(22) Filed: Jan. 17, 2001

(65) Prior Publication Data
US 2001/0016596 A1 Aug. 23, 2001

(30) Foreign Application Priority Data
Jan. 19, 2000 (DE) .......................................... 100 01 879

(51) Int. Cl.$^7$ ................... C07D 213/02; A01K 31/4164
(52) U.S. Cl. .................. 514/399; 548/267.4; 548/336.1
(58) Field of Search ...................... 546/332; 548/336.1, 548/375.1, 561, 267.4; 514/399

(56) References Cited

U.S. PATENT DOCUMENTS

| | | |
|---|---|---|
| 5,719,169 A | 2/1998 | Kleemann et al. |
| 5,744,641 A | 4/1998 | Gericke et al. |
| 5,753,680 A | 5/1998 | Gericke et al. |
| 5,840,761 A | 11/1998 | Gericke et al. |
| 5,965,744 A | 10/1999 | Weichert et al. |
| 6,001,881 A | 12/1999 | Weichert et al. |

FOREIGN PATENT DOCUMENTS

| | | |
|---|---|---|
| EP | 0 556 673 | 8/1993 |
| EP | 0 640 588 | 3/1995 |
| EP | 0 640 593 | 3/1995 |
| EP | 0 699 663 | 3/1996 |
| EP | 0 699 666 | 3/1996 |
| EP | 0 758 644 | 2/1997 |
| EP | 0 794 172 | 9/1997 |
| EP | 0 810 207 | 12/1997 |
| EP | 0 814 077 | 12/1997 |

OTHER PUBLICATIONS

European Search Report of Mar. 29, 2001.
Derwent Abstract of EP 810207.
Derwent Abstract of EP 794172.
Derwent Abstract of EP 556673.

*Primary Examiner*—Robert Gerstl

(57) ABSTRACT

Benzoylguanidines of the formula (I)

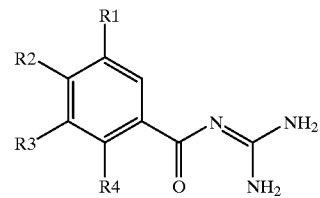

in which R1 to R4 have the meanings given in the specification and claims are suitable as antiarrhythmic medicaments having a cardioprotective component for infarct prophylaxis and infarct treatment and for the treatment of angina pectoris. The compounds of the invention also preventively inhibit the pathophysiological processes in the formation of ischemically induced damage, in particular in the triggering of ischemically induced cardiac arrhythmias.

20 Claims, No Drawings

SUBSTITUTED BENZOYLGUANIDINES, PROCESS FOR THEIR PREPARATION, THEIR USE AS A MEDICAMENT OR DIAGNOSTIC, AND MEDICAMENT CONTAINING THEM

The invention relates to benzoylguanidines of the formula (I)

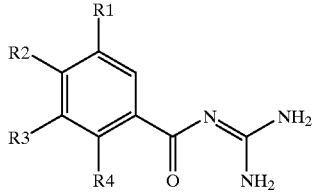

in which:
R1 is hydrogen, F, Cl, Br, I, $NO_2$, CN, $—X_o—(CH_2)_p—(CF_2)_q—CF_3$, $R5—SO_m—$, $R6—CO—$, $R6R7N—CO—$ or $R6R7N—SO_2—$;
X is oxygen, —S— or NR14;
m is zero, 1 or 2;
o is zero or 1;
p is zero, 1 or 2;
q is zero, 1, 2, 3, 4, 5 or 6;
R5 and R6
independently of one another are $(C_1–C_8)$-alkyl, $(C_3–C_6)$-alkenyl, $—C_nH_{2n}—R8$ or $CF_3$;
n is zero, 1, 2, 3 or 4;
R8 is $(C_3–C_7)$-cycloalkyl, or phenyl
which is not substituted or is substituted by 1 to 3 substituents selected from the group consisting of F, Cl, $CF_3$, methyl, methoxy and NR9R10;
R9 and R10 are
H or $(C_1–C_4)$-alkyl;
or
R6 is hydrogen;
R7 is hydrogen or $(C_1–C_4)$-alkyl;
or
R6 and R7
together can be 4 or 5 methylene groups, of which one $CH_2$ group can be replaced by oxygen, S, NH, N—$CH_3$ or N-benzyl;
R2 is $—Y-p-(C_6H_4)—R11$, $—Y-m-(C_6H_4)—R11$ or $—Y-o-(C_6H_4)—R11$;
R11 is $(C_1–C_9)$-heteroaryl which is linked via C or N and which is unsubstituted or substituted by 1 to 3 substituents selected from the group consisting of F, Cl, $CF_3$, $CH_3$, methoxy, hydroxyl, amino, methylamino, dimethylamino and benzyl;
Y is oxygen, —S— or NR12;
R12 is H or $(C_1–C_4)$-alkyl;
R3 is defined as R1;
or
R3 is $(C_1–C_6)$-alkyl or $—X—R13$;
X is oxygen, —S— or NR14;
R14 is
H or $(C_1–C_3)$-alkyl;
R13 is
H, $(C_1–C_6)$-alkyl, $(C_3–C_8)$-cycloalkyl or $—C_bH_{2b}—R15$;
b is zero, 1, 2, 3 or 4;
R15 is
phenyl which is unsubstituted or substituted by 1–3 substituents selected from the group consisting of F, Cl, $CF_3$, methyl, methoxy and NR9R10;
R9 and R10 are
H or $(C_1–C_4)$-alkyl;
or
R13 and R14
together are 4 or 5 methylene groups, of which one $CH_2$ group can be replaced by oxygen, S, NH, N—$CH_3$ or N-benzyl;
R4 is F, Cl, Br, I or $(C_1–C_4)$-alkyl;
as well as pharmaceutically tolerated salts thereof.

Another embodiment of the invention comprises compounds of the formula (I) in which:
R1 is hydrogen, F, Cl, CN, $CF_3$, $R5—SO_m—$, $R6—CO—$, $R6R7N—CO—$ or $R6R7N—SO_2—$;
m is zero, 1 or 2;
R5 and R6
independently of one another are $(C_1–C_8)$-alkyl, $(C_3–C_4)$-alkenyl, $—C_nH_{2n}—R8$ or $CF_3$;
n is zero or 1;
R8 is $(C_3–C_6)$-cycloalkyl or phenyl,
which is not substituted or is substituted by 1 to 3 substituents selected from the group consisting of F, Cl, $CF_3$, methyl, methoxy and NR9R10;
R9 and R10 are
H or methyl;
or
R6 is hydrogen;
R7 is hydrogen or methyl;
R2 is $—Y-p-(C_6H_4)—R11$, $—Y-m-(C_6H_4)—R11$ or $—Y-o-(C_6H_4)—R11$;
R11 is $(C_1–C_9)$-heteroaryl which is linked via C or N and which is unsubstituted or substituted by 1 to 3 substituents selected from the group consisting of F, Cl, $CF_3$, $CH_3$, methoxy, hydroxyl, amino, methylamino, dimethylamino and benzyl;
Y is oxygen, —S— or NR12;
R12 is H or $(C_1–C_4)$-alkyl;
R3 is hydrogen, methyl, CN, $CF_3$, F or Cl;
R4 is F, Cl or $(C_1–C_4)$-alkyl;
as well as pharmaceutically tolerated salts thereof.

Yet another embodiment of the invention comprises compounds of formula (I) in which:
R1 is hydrogen, F, Cl, CN, $CF_3$ or $R5—SO_m—$;
m is zero, 1 or 2;
R5 is
methyl or $CF_3$;
R2 is $—Y-p-(C_6H_4)—R11$, $—Y-m-(C_6H_4)—R11$ or $—Y-o-(C_6H_4)—R11$;
R11 is $(C_1–C_9)$-heteroaryl which is linked via C or N and which is unsubstituted or substituted by 1 to 2 substituents selected from the group consisting of F, Cl, $CF_3$, $CH_3$, methoxy, dimethylamino and benzyl;
Y is oxygen;
R3 is hydrogen, methyl, CN, $CF_3$, F or Cl;
R4 is $(C_1–C_4)$-alkyl;
as well as pharmaceutically tolerated salts thereof.

Other embodiments of the invention are compounds of the formula (I) in which:
R1 is hydrogen, F, Cl, CN, $CF_3$ or $R5—SO2—$;
R5 is methyl or $CF_3$;

R2 is —Y-p-($C_6H_4$)—R11, —Y-m-($C_6H_4$)—R11 or —Y-o-($C_6H_4$)—R11;
   R11 is ($C_1$–$C_5$)-heteroaryl which is linked via C or N and which is unsubstituted or substituted by 1 to 2 substituents selected from the group consisting of F, Cl, $CF_3$, $CH_3$, methoxy, dimethylamino and benzyl;
Y is oxygen;
R3 is hydrogen;
R4 is ($C_1$–$C_4$)-alkyl;
as well as pharmaceutically tolerated salts thereof.

Still other embodiments of the invention encompass compounds of the formula (I) in which:
R1 is $CF_3$;
R2 is —Y-p-($C_6H_4$)—R11, —Y-m-($C_6H_4$)—R11 or —Y-o-($C_6H_4$)—R11;
   R11 is imidazolyl or triazolyl which in each case is unsubstituted or substituted by 1 to 2 substituents selected from the group consisting of F, Cl, $CF_3$, $CH_3$, methoxy, dimethylamino and benzyl;
Y is oxygen;
R3 is hydrogen;
R4 is methyl;
as well as pharmaceutically tolerated salts thereof.

All alkyl radicals can be either straight-chain or branched.

($C_1$–$C_9$)-heteroaryl is understood to mean radicals which are derived from phenyl or naphthyl, in which one or more CH groups are replaced by N, and/or in which at least two neighboring CH groups are replaced by S, NH, or O (with the formation of a five-membered aromatic ring). In addition, one or both atoms of the fusion site of bicyclic radicals (as in indolizinyl) can also be N atoms.

Heteroaryl may be furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl or cinnolinyl; particularly furanyl, thienyl, pyrrolyl, imidazolyl, pyrazolyl, triazolyl, thiazolyl, pyridyl, indolyl, quinolyl, and isoquinolyl.

The invention furthermore relates to processes for preparing the compound I, which comprises reacting a compound of the formula (II)

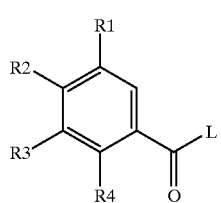

(II)

where R1 to R4 have the meanings given above, and L is a leaving group which can readily be substituted nucleophilically, with guanidine.

The activated acid derivatives of the formula (II), in which L is an alkoxy group, such as a methoxy group, a phenoxy group, a phenylthio, methylthio or 2-pyridylthio group, or a nitrogen heterocycle, e.g., 1-imidazolyl, are advantageously obtained, in a manner known in the art, from the underlying carbonyl chlorides (formula (II), L=Cl), which, for their part, can in turn be prepared, in a manner known in the art, from the underlying carboxylic acids (formula (II), L=OH), for example, using thionyl chloride.

In addition to the carbonyl chlorides of the formula (II) (L=Cl), further activated acid derivatives of the formula (II) can also be prepared, in a manner known in the art, directly from the underlying benzoic acid derivatives (formula (II), L=OH). Such activated acid derivatives include the methyl esters of the formula (II) where L=$OCH_3$, prepared by treating with gaseous HCl in methanol; the imidazolides of the formula (II), prepared by treating with carbonyldiimidazole (L=1-imidazolyl, Staab, *Angew. Chem. Int. Ed. Engl.* 1, 351–367 (1962)); the mixed anhydrides II, prepared with Cl—$COOC_2H_5$ or tosyl chloride in the presence of triethylamine in an inert solvent; as well as the activation of benzoic acids with dicyclohexylcarbodiimide (DCC) or with O-[(cyano(ethoxycarbonyl)methylene)amino]-1,1,3,3-tetramethyluronium tetrafluoroborate ("TOTU") (Proceedings of the 21st European Peptide Symposium, Peptides 1990, Editors E. Giralt and D. Andreu, Escom, Leiden, 1991). A series of suitable methods for preparing activated carboxylic acid derivatives of the formula (II) are given, with citation of the source literature, in J. March, *Advanced Organic Chemistry*, Third Edition (John Wiley & Sons, 1985), p. 350.

The reaction of an activated carboxylic acid derivative of the formula (II) with guanidine is effected, in a manner known per se, in a protic or aprotic organic solvent which is polar but inert. In this context, methanol, isopropanol or THF have proven to be suitable, at temperatures of from 20° C. up to the boiling temperature of these solvents, for use in the reaction of the methyl benzoates (formula (II), L=OMe) with guanidine. Aprotic, inert solvents, such as THF, dimethoxyethane and dioxane, were advantageously employed in most of the reactions of compounds of formula (II) with salt-free guanidine. However, while employing a base, such as, for example, NaOH, water can also be used as solvent in reactions of compounds of formula (II) with guanidine.

When L=Cl, an acid scavenger, e.g., in the form of excess guanidine, is advantageously added in order to bind the hydrohalic acid.

Some of the underlying benzoic acid derivatives of the formula (II) are known and are described in the literature. The unknown compounds of the formula (II) may be prepared by methods known from the literature. The resulting benzoic acids are reacted to give compounds of formula (I) according to the invention in accordance with one of the above-described process variants.

The introduction of some substituents in the 2, 3, 4 and 5 positions is achieved by methods known from the literature involving palladium-mediated cross-coupling of aryl halides or aryl triflates with, for example, organostannanes, organoboronic acids, organoboranes, organocopper compounds, or organozinc compounds.

Benzoylguanidines of formula (I) are in general weak bases and are able to bind acid with the formation of salts. Salts of all pharmacologically tolerated acids, for example, halides (such as hydrochlorides), lactates, sulfates, citrates, tartrates, acetates, phosphates, methylsulfonates and p-toluenesulfonates, are suitable acid addition salts.

Compounds of formula (I) are substituted acylguanidines.

Compounds similar to the compounds of formula (I) are disclosed in European Laid-Open Specification 640 593 (HOE 93/F 220). However, these always contain other substituents in the R4 position (ortho position); the compounds according to the invention are neither mentioned nor suggested therein.

In comparison with the known compounds, the compounds according to the invention are distinguished by an extremely high activity in the inhibition of $Na^+/H^+$ exchange, and by an improved solubility in water.

Similarly to some known compounds, the inventive compounds have no undesirable and/or disadvantageous salidiuretic properties, but, unlike known compounds, have very good antiarrhythmic properties. Such properties are important, for example, for the treatment of illnesses which occur in the case of symptoms of oxygen deficiency. As a result of their pharmacological properties, the compounds of the invention are outstandingly suitable as antiarrhythmic medicaments having a cardioprotective component for infarct prophylaxis and infarct treatment and for the treatment of angina pectoris, where they also preventively inhibit or greatly decrease the pathophysiological processes in the formation of ischemically induced damage, in particular in the triggering of ischemically induced cardiac arrhythmias. Because of their protective actions against pathological hypoxic and ischemic situations, the compounds of the formula (I) according to the invention can be used, as a result of inhibition of the cellular $Na^+/H^+$ exchange mechanism, as medicaments for the treatment of all acute or chronic damage caused by ischemia or illnesses primarily or secondarily induced thereby. This relates to their use as medicaments for surgical interventions, e.g. in organ transplantation, where the compounds can be used both for the protection of the organs in the donor before and during removal, for the protection of removed organs, for example during treatment with or storage thereof in physiological bath fluids, and also during transfer to the recipient's body.

The compounds are likewise valuable medicaments having a protective action when carrying out angioplastic surgical interventions, for example on the heart and on peripheral vessels. Corresponding to their protective action against ischemically induced damage, the compounds are also suitable as medicaments for the treatment of ischemias of the nervous system, in particular of the CNS, where they are suitable, for example, for the treatment of stroke or of cerebral edema. Moreover, the compounds of the formula (I) according to the invention are likewise suitable for the treatment of forms of shock, such as allergic, cardiogenic, hypovolemic, and bacterial shock.

The compounds of the formula (I) according to the invention are moreover distinguished by strong inhibitory action on the proliferation of cells, for example, fibroblast cell proliferation and the proliferation of vascular smooth muscle cells. The compounds of the formula (I) are therefore suitable as valuable therapeutics for illnesses in which cell proliferation is a primary or secondary cause, and can therefore be used as antiatherosclerotics, agents against diabetic late complications, carcinomatous disorders, fibrotic disorders such as pulmonary fibrosis, liver fibrosis or kidney fibrosis, organ hypertrophy and hyperplasia, in particular in prostate hyperplasia and prostate hypertrophy.

The compounds according to the invention are effective inhibitors of the cellular sodium-proton antiporter ($Na^+/H^+$ exchanger), which is implicated in numerous disorders (essential hypertension, atherosclerosis, diabetes, etc.) and even in those cells which are readily accessible to measurement, such as, for example, in erythrocytes, platelets or leukocytes. The compounds according to the invention are therefore suitable as outstanding and simple scientific tools, for example, in their use as diagnostics for the determination and differentiation of certain forms of hypertension, but also of atherosclerosis, diabetes, proliferative disorders, etc. Moreover, the compounds of the formula (I) are suitable for therapy for the prevention of the origination of high blood pressure, for example, in the prevention or treatment of essential hypertension.

It has moreover been found that compounds of the formula (I) have a favorable effect on serum lipoproteins. It is generally recognized that excessively high blood fat values, so-called hyperlipoproteinemias, are a significant risk factor for the origination of arteriosclerotic vascular changes, in particular of coronary heart disease. For the prophylaxis and the regression of atherosclerotic changes, the lowering of raised serum lipoproteins has extraordinary importance. In addition to the reduction of the total serum cholesterol, the lowering of the proportion of specific atherogenic lipid fractions of this total cholesterol, in particular the low density lipoproteins (LDL) and the very low density lipoproteins (VLDL) has particular importance, as these lipid fractions are an atherogenic risk factor. However, high density lipoproteins are ascribed a protective function against coronary heart disease. Accordingly, hypolipidemics should be able to lower not only the total cholesterol, but in particular the VLDL and LDL serum cholesterol fractions.

It has now been found that compounds of the formula (I) exhibit valuable therapeutically utilizable properties with respect to influencing the serum lipid levels. Thus, compounds of the invention significantly lower the increased serum concentration of LDL and VLDL, such as are observed, for example, due to increased dietetic intake of a cholesterol- and lipid-rich diet or in pathological metabolic changes, for example, in genetically related hyperlipidemias. They can therefore be used for the prophylaxis and for the regression of atherosclerotic changes by eliminating a causal risk factor. These include not only the primary hyperlipidemias, but also certain secondary hyperlipidemias, such as occur, for example, in diabetes.

Moreover, the compounds of the formula (I) lead to a marked reduction of infarcts induced by metabolic anomalies and in particular to a significant decrease in the infarct size and its degree of severity. Compounds of the formula (I) furthermore lead to an effective protection against endothelial damage induced by metabolic anomalies. With this protection of the vessels against the endothelial dysfunction syndrome, compounds of the formula (I) are valuable medicaments for the prevention and for the treatment of coronary vasospasms, atherogenesis and atherosclerosis, left-ventricular hypertrophy, dilated cardiomyopathy, and thrombotic disorders.

The inventive compounds therefore are useful in medicaments for the treatment of hypercholesteremia; for the prevention of atherogenesis; for the prevention and treatment of atherosclerosis, for the prevention and treatment of illnesses which are caused by increased cholesterol levels, for the prevention and treatment of illnesses which are caused by endothelial dysfunction, for the prevention and treatment of iatherosclerosis-induced hypertension, for the prevention and treatment of atherosclerosis-induced thromboses, for the prevention and treatment of hypercholesteremia and endothelial dysfunction of induced ischemic damage and post-ischemic reperfusion damage, for the prevention and treatment of hypercholesteremia and endothelial dysfunction of induced cardiac hypertrophies and cardiomyopathies, and for the prevention and treatment of hypercholesteremia and endothelial dysfunction of induced coronary vasospasms and myocardial infarcts.

In addition, compounds of the invention are useful in medicaments for the treatment of the illnesses mentioned previously in combination with hypotensive substances, preferably with angiotensin converting enzyme (ACE) inhibitors and angiotensin receptor antagonists; a combination of at least one compound of the formula (I) which is an NHE inhibitor with an active compound lowering the blood fat level, preferably with an HMG-CoA reductase inhibitor (e.g., lovastatin or pravastatin), where the latter produces a hypolipidemic action and thereby increases the hypolipidemic properties of the NHE inhibitor of the formula (I). This combination is favorable because it has increased action and with a decreased amount of active compound.

The administration of sodium-proton exchange inhibitors of the formula (I) as novel medicaments for lowering increased blood fat levels is claimed, as well as the combination of sodium-proton exchange inhibitors with hypotensive medicaments and/or medicaments having a hypolipidemic action.

In this context, medicaments containing at least one compound of formula (I) can be administered orally, parenterally, intravenously, or rectally, or by inhalation, the preferred route of administration being dependent on how the disorder manifests itself. In this context, the inventive compounds may be used alone, or together with pharmaceutical excipients, both for veterinary and human medicine.

Owing to his specialist knowledge, the person skilled in the art is familiar with which excipients are suitable for the desired pharmaceutical formulation. In addition to solvents, gel formers, suppository bases, tablet excipients, and other active-compound carriers, it is possible to use, for example, antioxidants, dispersants, emulsifiers, defoamers, taste corrigents, preservatives, solubilizers or colorants.

In order to prepare a formulation for oral use, the active compounds are mixed with the additives which are suitable for the purpose, such as vehicles, stabilizers or inert diluents, and converted by customary methods into forms suitable for administration, such as tablets, coated tablets, hard gelatin capsules or aqueous, alcoholic or oily solutions. Gum arabic, magnesia, magnesium carbonate, potassium phosphate, lactose, glucose, or starch, for example, corn starch, can be used as inert carriers. In this context, the preparation can be effected as dry or wet granules. Vegetable or animal oils, for example, such as sunflower oil or cod-liver oil, are suitable for use as oily vehicles or as solvents.

For subcutaneous or intravenous administration, the active compounds, if desired together with the substances which are customary for the purpose, such as solubilizers, emulsifiers or additional excipients, are brought into solution, suspension, or emulsion. Examples of suitable solvents are: water, physiological saline solution, or alcohol, for example ethanol, propanol or glycerol, and in addition sugar solutions, such as glucose or mannitol solutions, or mixtures of these different solvents.

Solutions, suspensions, or emulsions of the active compound of the formula (I) in a pharmaceutically harmless solvent, such as, ethanol or water, or a mixture of such solvents, are suitable for use as a pharmaceutical formulation for administration in the form of aerosols or sprays.

If required, the formulation can contain additional pharmaceutical excipients, such as surfactants, emulsifiers, or stabilizers, as well as a propellant. Such a preparation customarily contains the active compound in a concentration of about 0.1 to 10%, for example, about 0.3 to 3%, by weight.

The dosage of the active compound of the formula (I) to be administered, and the frequency of the administration, depend on the potention and the duration of action of the compounds used. The dosage to be used depends additionally on the nature and severity of the illness to be treated, as well as on the sex, age, weight and individual responsiveness of the mammal to be treated.

On average, the minimum daily dose of a compound of the formula (I) for a patient of about 75 kg in weight is at least 0.001 mg/kg, but may be at least 0.01 mg/kg, or at least 0.1 mg/kg. On average, the maximum daily dose of a compound of the formula (I) is preferably about 1 mg/kg, but may be up to 10 mg/kg, of body weight. In acute episodes of illness, for example immediately after suffering a cardiac infarction, even higher, and/or more frequent, dosages may also be necessary, e.g., up to 4 individual doses per day. In association with i.v. use, for example in the case of an infarction patient in intensive care, up to 200 mg per day may be necessary.

List of abbreviations:
CDI carbonyidiimidazole
MeOH methanol
DMF N,N-dimethylformamide
RT room temperature
EA ethyl acetate (EtOAc)
eq equivalent
ES electrospray ionization Experimental Section

EXAMPLE 1

4-[(Imidazol-1-yl)phenoxy]-2-methyl-5-trifluoromethylbenzoylguanidine Dihydrochloride,
Colorless Solid, $M^++H$ (ES)=404

Synthetic Route:

a) Methyl 4-[(imidazol-1-yl)phenoxy]-2-methyl-5-trifluoromethylbenzoate was obtained by reacting methyl 4-fluoro-2-methyl-3-trifluoromethylbenzoate with 1 eq of 4-(imidazol-1-yl)phenol in the presence of 4 eq of potassium carbonate in DMF at 120° C. over the course of 16 h. After evaporation of the solvent, the residue was subjected to aqueous work-up and extracted by shaking with EA. The solvent was dried and then evaporated, yielding colorless oil, $M^+(ES)=376$.

b) 4-[(imidazol-1-yl)phenoxy]-2-methyl-5-trifluoromethylbenzoic acid was then obtained by basic hydrolysis using an excess of 2N NaOHaq in MeOH at RT over the course of 2 h. After acidification with 2N HCl, extraction with EA followed. After drying of the solvent, followed by evaporation, a colorless oil was obtained, $M^+(ES)=362$.

4-[(imidazol-1-yl)phenoxy]-2-methyl-5-trifluoromethylbenzoylguanidine dihydrochloride was then obtained by activation with 2 eq of CDI in DMF and subsequent reaction with 6 eq of guanidinium hydrochloride in the presence of 7 eq of diisopropylethylamine at RT over the course of 3 h. After removal of the solvent, preparative HPLC ($CH_3CN/H_2O$) was carried out, followed by salt formation with ethereal hydrochloric acid.

EXAMPLE 2

4-(Triazol-1-yl)phenoxy-2-methyl-3-trifluoromethylbenzoylguanidine Bistrifluoroacetate,
Colorless Solid, $M^+H$ (ES)=405

Synthetic Route:

a) Methyl 4-[(triazol-1-yl)phenoxy]-2-methyl-5-trifluoromethylbenzoate was prepared analogously to Example 1 a) by reaction with 1 eq of 4-(triazol-1-yl)phenol, producing a colorless oil, $M^+(ES)=377$.

b) 4-[(Triazol-1-yl)phenoxy]-2-methyl-5-trifluoromethylbenzoic acid was prepared analogously to Example 1 b), producing a colorless oil, $M^+(ES)=363$.

c) 4-[(Triazol-1-yl)phenoxy]-2-methyl-5-trifluoromethylbenzoylguanidine bis-trifluoroacetate was prepared analogously to Example 1 c). The salt formation was then accomplished by means of trifluoroacetic acid.

The present invention may be embodied in other specific forms without departing from its spirit or essential characteristics. The described embodiments are to be considered in all respects as illustrative only and not restrictive. The scope of the present invention is, therefore, indicated by the appended claims rather than by the foregoing description. All changes which come within the meaning and range of equivalency of the claims are to be embraced within their scope.

We claim:

1. A benzoylguanidine of the formula (I)

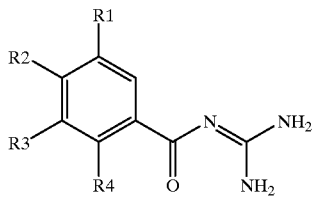

in which:
R1 is hydrogen, F, Cl, Br, I, $NO_2$, CN, —$X_o$—$(CH_2)_p$—$(CF_2)_q$—$CF_3$, R5—$SO_m$—, R6—CO—, R6R7N—CO—, or R6R7N—$SO_2$—;
X is oxygen, —S—, or NR14;
m is zero, 1, or 2;
o is zero or 1;
p is zero, 1, or 2;
q is zero, 1, 2, 3, 4, 5, or 6;
R5 and R6
each independently of one another are selected from ($C_1$–$C_8$)-alkyl, ($C_3$–$C_6$)-alkenyl, —$C_nH_{2n}$—R8, and $CF_3$;
n is zero, 1, 2, 3, or 4;
R8 is ($C_3$–$C_7$)-cycloalkyl, or phenyl
which is unsubstituted, or is substituted by 1 to 3 substituents each independently selected from F, Cl, $CF_3$, methyl, methoxy and NR9R10;
R9 and R10 are each independently selected from H and ($C_1$–$C_4$)-alkyl;
or
R6 is hydrogen;
R7 is hydrogen or ($C_1$–$C_4$)-alkyl;
or
R6 and R7
together can be 4 or 5 methylene groups, of which one methylene group is optionally replaced by oxygen, S, NH, N—$CH_3$, or N-benzyl;
R2 is —Y-p-($C_6H_4$)—R11, —Y-m-($C_6H_4$)—R11, or —Y-o-($C_6H_4$)—R11;
R11 is ($C_1$–$C_9$)-heteroaryl, which is linked via C or N and which is unsubstituted or substituted by 1 to 3 substituents each independently selected from F, Cl, $CF_3$, $CH_3$, methoxy, hydroxyl, amino, methylamino, dimethylamino, and benzyl;
Y is oxygen, —S—, or NR12;
R12 is H or ($C_1$–$C_4$)-alkyl;
R3 is defined as R1;
or
R3 is ($C_1$–$C_6$)-alkyl or —X—R13;
X is oxygen, —S— or NR14;
R14 is H or ($C_1$–$C_3$)-alkyl;
R13 is H, ($C_1$–$C_6$)-alkyl, ($C_3$–$C_8$)-cycloalkyl, or —$C_bH_{2b}$—R15;

b is zero, 1, 2, 3 or 4;
R15 is
phenyl which is unsubstituted or substituted by 1 to 3 substituents each independently selected from F, Cl, $CF_3$, methyl, methoxy, and NR9R10;
R9 and R10 are each independently selected from H and ($C_1$–$C_4$)-alkyl;
or
R13 and R14
together are 4 or 5 methylene groups, of which one methylene group is optionally replaced by oxygen, S, NH, N—$CH_3$, or N-benzyl;
R4 is F, Cl, Br, I, or $C_1$–$C_4$-alkyl;
or a pharmaceutically tolerated salt thereof.

2. A compound as claimed in claim 1, wherein:
R1 is hydrogen, F, Cl, CN, $CF_3$, R5—$SO_m$—, R6—CO—, R6R7N—CO—, or R6R7N—$SO_2$—;
m is zero, 1, or 2;
R5 and R6
each independently of one another are selected from ($C_1$–$C_8$)-alkyl, ($C_3$–$C_4$)-alkenyl, —$C_nH_{2n}$—R8, and $CF_3$;
n is zero or 1;
R8 is ($C_3$–$C_6$)-cycloalkyl or phenyl
which is unsubstituted, or is substituted by 1 to 3 substituents selected from F, Cl, $CF_3$, methyl, methoxy, and NR9R10;
R9 and R10 are H or methyl;
or
R6 is hydrogen;
R7 is hydrogen or methyl;
R2 is —Y-p-($C_6H_4$)—R11, —Y-m-($C_6H_4$)—R11, or —Y-o-($C_6H_4$)—R11;
R11 is ($C_1$–$C_9$)-heteroaryl which is linked via C or N and which is unsubstituted or substituted by 1 to 3 substituents each independently selected from F, Cl, $CF_3$, $CH_3$, methoxy, hydroxyl, amino, methylamino, dimethylamino, and benzyl;
Y is oxygen, —S—, or NR12;
R12 is H or ($C_1$–$C_4$)-alkyl;
R3 is hydrogen, methyl, CN, $CF_3$, F, or Cl;
R4 is F, Cl, or ($C_1$–$C_4$)-alkyl;
or a pharmaceutically tolerated salt thereof.

3. A compound as claimed in claim 1, wherein:
R1 is hydrogen, F, Cl, CN, $CF_3$ or R5—$SO_m$—;
m is zero, 1 or 2;
R5 is methyl or $CF_3$;
R2 is —Y-p-($C_6H_4$)—R11, —Y-m-($C_6H_4$)—R11 or —Y-o-($C_6H_4$)—R11;
R11 is ($C_1$–$C_9$)-heteroaryl which is linked via C or N and which is unsubstituted or substituted by 1 to 2 substituents each independently selected from the group consisting of F, Cl, $CF_3$, $CH_3$, methoxy, dimethylamino, and benzyl;
Y is oxygen;
R3 is hydrogen, methyl, CN, $CF_3$, F, or Cl;
R4 is ($C_1$–$C_4$)-alkyl;
or a pharmaceutically tolerated salt thereof.

4. A compound as claimed in claim 1, wherein:
R1 is hydrogen, F, Cl, CN, $CF_3$, or R5—$SO_2$—;
R5 is methyl or $CF_3$;
R2 is —Y-p-($C_6H_4$)—R11, —Y-m-($C_6H_4$)—R11, or —Y-o-($C_6H_4$)—R11;
R11 is ($C_1$–$C_5$)-heteroaryl which is linked via C or N and which is unsubstituted, or substituted by 1 to 2 substituents each independently selected from F, Cl, $CF_3$, $CH_3$, methoxy, dimethylamino and benzyl;
Y is oxygen;
R3 is hydrogen;
R4 is $(C_1–C_4)$-alkyl;
or a pharmaceutically tolerated salt thereof.

5. A compound as claimed in claim 1, wherein:
R1 is $CF_3$;
R2 is —Y-p-$(C_6H_4)$—R11, —Y-m-$(C_6H_4)$—R11 or —Y-o-$(C_6H_4)$—R11;
R11 is imidazolyl or triazolyl, unsubstituted, or substituted by 1 to 2 substituents each independently selected from F, Cl, $CF_3$, $CH_3$, methoxy, dimethylamino, and benzyl;
Y is oxygen;
R3 is hydrogen;
R4 is methyl;
or a pharmaceutically tolerated salt thereof.

6. A process for preparing of a compound of formula (I), comprising reacting a compound of formula (II)

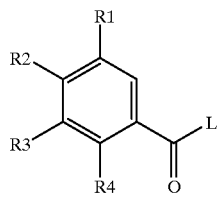

(II)

wherein R1 to R4 are defined as in claim 1, and L is a leaving group which can readily be substituted nucleophilically, with guanidine.

7. A method of treating or preventing illness caused by ischemic conditions, comprising administering to a patient in need thereof an effective amount of a compound as claimed in claim 1.

8. A method of treating or preventing cardiac infarction or arrhythmias, comprising administering to a patient in need thereof an effective amount of a compound as claimed in claim 1.

9. A method of treating or preventing angina pectoris, comprising administering to a patient in need thereof an effective amount of a compound as claimed in claim 1.

10. A method of treating or preventing ischemic conditions of the heart, comprising administering to a patient in need thereof an effective amount of a compound as claimed in claim 1.

11. A method of treating or preventing ischemic conditions of the peripheral and central nervous system and of stroke, comprising administering to a patient in need thereof an effective amount of a compound as claimed in claim 1.

12. A method of treating or preventing ischemic conditions of peripheral organs and limbs, comprising administering to a patient in need thereof an effective amount of a compound as claimed in claim 1.

13. A method of treating or preventing conditions of shock, comprising administering to a patient in need thereof an effective amount of a compound as claimed in claim 1.

14. A method of preventing damage by ischemia during a surgical intervention, comprising administering to at least one of a donor, an organ, and a patient of the surgical intervention an effective amount of a compound as claimed in claim 1.

15. The method of claim 14, wherein the surgical intervention is an organ transplantation.

16. A method of preserving or storing a transplant organ, comprising administering an effective amount of a compound as claimed in claim 1 to the organ.

17. The method of claim 16, wherein administering to the organ occurs via a physiological bath fluid.

18. A method of treating or preventing illnesses in which cell proliferation is a primary or secondary cause, comprising administering to a patient in need thereof an effective amount of a compound as claimed in claim 1.

19. A method of treating or preventing disorders of fat metabolism, comprising administering to a patient in need thereof an effective amount of a compound as claimed in claim 1.

20. A pharmaceutical composition, comprising an effective amount of at least one compound as claimed in any one of claims 1 to 4 and a suitable excipient.

* * * * *